United States Patent [19]

Abou-Gharbia et al.

[11] Patent Number: 4,937,347
[45] Date of Patent: Jun. 26, 1990

[54] POLYCYCLICAMINE WITH PSYCHOTROPIC ACTIVITY

[75] Inventors: Magid A. Abou-Gharbia, Wilmington, Del.; Usha R. Patel, Audubon, Pa.

[73] Assignee: American Home Products Corporation, New York, N.Y.

[21] Appl. No.: 348,323

[22] Filed: May 5, 1989

Related U.S. Application Data

[62] Division of Ser. No. 119,530, Nov. 12, 1987, Pat. No. 4,855,430.

[51] Int. Cl.⁵ .................. C07D 401/06; C07D 405/14
[52] U.S. Cl. .................................... 546/272; 544/284; 544/295; 544/357; 544/364; 544/373; 546/176; 546/270; 546/269
[58] Field of Search ....................... 546/269, 270, 272

[56] References Cited

U.S. PATENT DOCUMENTS 3,133,061  5/1964  Kirchner ............................ 540/597
3,377,353  4/1968  Bruce ................................. 546/200
3,378,566  4/1968  Mohrbacher et al. .............. 546/200

OTHER PUBLICATIONS

McNeil Lab; Inc., Chem. Abst. 64-3495c (1966).
Poos et al., Chem. Abst. 65-3828g (1966).
Bruce, Chem. Abst. 69-67151t (1968).
Abou-Gharbia et al., Chem. Abst. 110-94996u (1989).

Primary Examiner—Cecilia Shen
Attorney, Agent, or Firm—George Tarnowski

[57] ABSTRACT

These are disclosed compounds of the formula

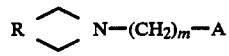

wherein R represents

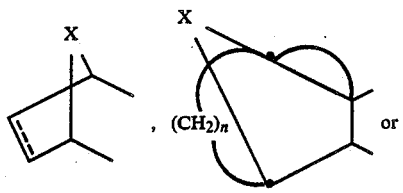

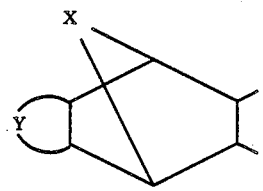

where
X is lower alkylene, vinylene or O;
Y is lower alkylene or vinylene;
the dotted line represents an optional double bond;
m is 1-3;
n is 2-4;
A is phenyl, benzoyl, pyridinyl, quinolinyl or quinoxalinyl, or any of the foregoing substituted with lower alkyl, lower alkoxy, halo, cyano, nitro or trifluoromethyl; or when m is >1, A represents the grouping

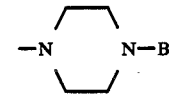

where
B is phenyl, pyrimidinyl, pyridinyl or pyrazinyl, or any of the foregoing substituted with lower alkyl, lower alkoxy, halo, cyano, nitro or trifluoromethyl, with the proviso that where R is

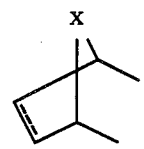

A is other than unsubstituted or substituted benzoyl or pyridinyl;

and the pharmacologically acceptable salts thereof and their use as antipsychotic/anxiolytic and antidepressant agents and in the treatment of sexual dysfunction and having a low liability for extrapyramidal side effects.

4 Claims, No Drawings

POLYCYCLICAMINE WITH PSYCHOTROPIC ACTIVITY

This is a division of application Ser. No. 119,530, filed Nov. 12, 1987 now U.S. Pat. No. 4,855,430.

This invention relates to novel compounds having utility in the treatment of central nervous systems disorders such as anxiety, psychosis, depression and sexual dysfunction.

Recent research has provided a growing body of literature which attributes the activity of some of the newer classes of CNS agents to their selective activation of the serotonin receptor subtype designated the 5-HT$_{1A}$ receptor. This has been the case especially for compounds such as buspirone (8-[4-[4-(2-pyrimidinyl)-1-piperazinyl]butyl]-8-azaspiro[4.5]decane-7,9-dione) and TVX Q 7821 (2-[4-[4-(2-pyrimidinyl)-1-piperazinyl]butyl]-1,2-benzisothiazol-3-(2H)one 1,1-dioxide hydrochloride). See Eison et al., *Pharmacol. Biochem. and Behav.*, 24, 701 (1986); Dompert et al., *NaunynSchmiedeberg Arch. Pharmacol.*, 328, 467 (1985) and Spencer and Traber, *Psychopharmacol.*, 91, 25 (1987). Both of the compounds cited above are anxiolytics which demonstrate binding at the 5-HT$_{1A}$ site, while other classic anxiolytics, such as the benzodiazepines and pentobarbital, do not act via the 5-HT$_{1A}$ receptor. Moreover, compounds such as TVX Q 7821 have been found to possess antidepressant activity (see West German Patent Application No. 3,321,969A) while buspirone has been found to be useful in the treatment of sexual dysfunction (see U.S. Pat. No. 4,640,921).

Accordingly, buspirone-like compounds activating the 5-HT$_{1A}$ receptor site, such as those of the present invention, are useful as anxiolytics/antipsychotics, antidepressants and in the treatment of sexual dysfunction.

The compounds of the invention are characterized by the formula

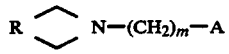

wherein R represents

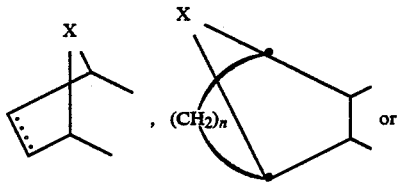

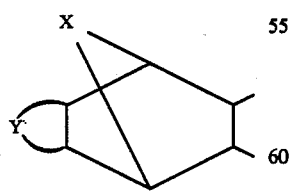

where
X is lower alkylene, vinylene or O;
Y is lower alkylene or vinylene;
the dotted line represents an optional double bond;
m is 1–3;
n is 2–4;

A is phenyl, benzoyl, pyridinyl, quinolinyl or quinoxalinyl, or any of the foregoing substituted with lower alkyl, lower alkoxy, halo, cyano, nitro or trifluoromethyl; or when m is >1, A represents the grouping

where
B is phenyl, pyrimidinyl, pyridinyl or pyrazinyl, or any of the foregoing substituted with lower alkyl, lower alkoxy, halo, cyano, nitro or trifluoromethyl, with the proviso that were R is

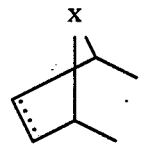

A is other than unsubstituted or substituted benzoyl or pyridinyl;
and the pharmacologically acceptable salts thereof.

The term "lower alkyl" refers to moieties having 1–6 carbon atoms in the carbon chain. The term "lower alkylene" refers to moieties having 1–4 carbon atoms in the carbon chain. The term "lower alkoxy" refers to moieties having 1–6 carbon atoms. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods. Thus, compounds in which R is

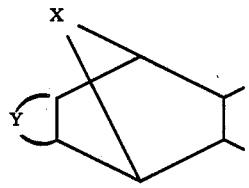

can be prepared, for example, by reacting maleimide with an appropriate diene, e.g. 1,3,5,7-cyclooctatetraene, to yield a precursor which when reduced with LiAlH$_4$ in tetrahydrofuran yields a polycyclic amine intermediate:

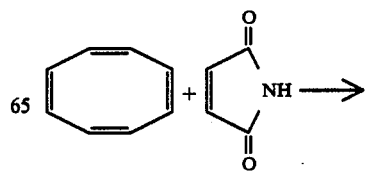

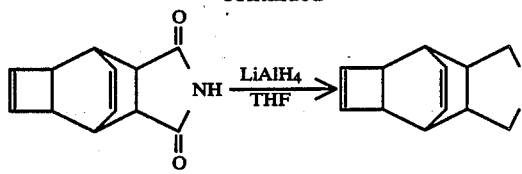

This intermediate product can then be reacted with, for example, an appropriately substituted 4-piperazinylalkylhalide to yield the desired final product:

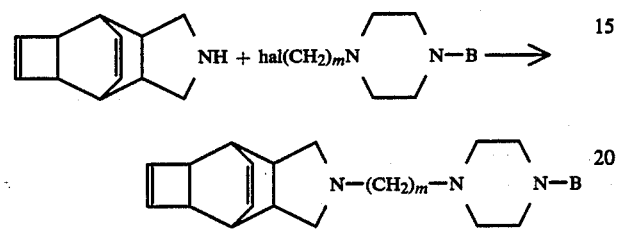

In the alternative, the polycyclic amine intermediate can be reacted with a suitable dihalo lower alkane, followed by reaction with a suitable A-substituent starting material:

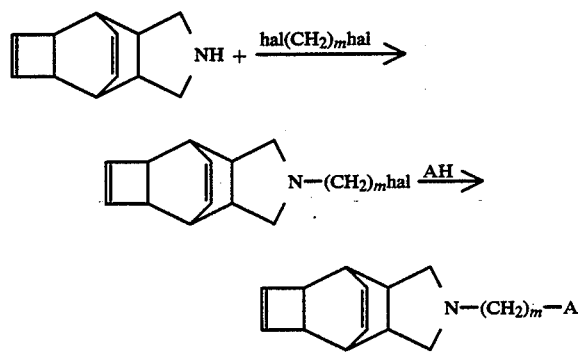

In the above sequences, B, A and m are as defined hereinbefore and hal is a halo atom, such as chloro or bromo.

The above reaction sequences can also be used to prepare compounds with other R moieties. Thus, by selecting a diene of appropriate ring size and degree of unsaturation, it is possible to prepare other polycyclic amine intermediates:

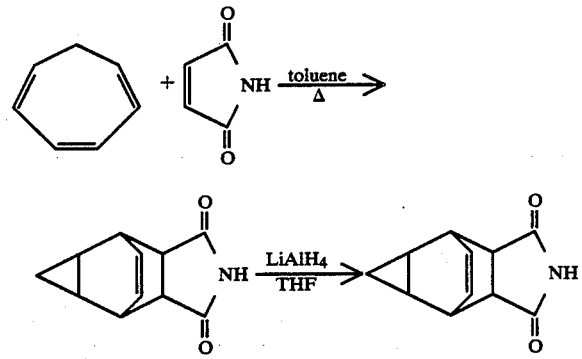

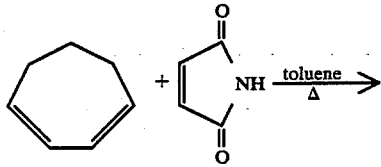

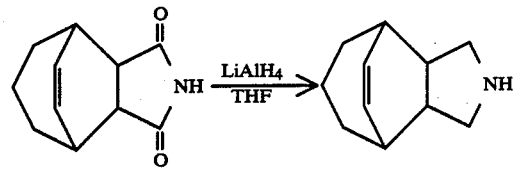

In yet another alternative preparative sequence, maleimide can first be reacted with a dihalo lower alkane followed by reaction with an appropriate A substituent-containing starting material to yield the following intermediate:

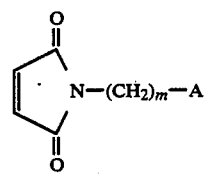

which can then be further subjected to Diels-Alder addition with appropriate reactants and after reduction yields desired final products.

The saturated analogs of the compounds discussed in all of the previous preparative schemes can be prepared by hydrogenating the intermediates or the final products using hydrogen and Pd/C as a catalyst.

Some of the starting polycyclic amine intermediates useful in preparing the compounds of the invention can be obtained commercially. Thus, the compound 3-azabicyclo[3.2.2]nonane is commercially available and can be used directly to prepare the desired final products. All other starting materials used in the above-described preparative routes are commercially available or can be made according to procedures taught in the chemical literature.

Of course, other methods of preparation, which will occur to those skilled in the art, may also be employed to prepare the compounds of the invention.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display preclinical antipsychotic activity without or with minimal side effects. Moreover, based on their buspirone-like profile, the compounds of the invention can be considered of clinical value in treating anxiety neuroses, depression as well as sexual dysfunction.

When employed as anxiolytics/antipsychotics, antidepressants or in treating sexual dysfunction, the effective dosage of the substances active for such treatment will vary according to the particular compound being employed, the severity and nature of condition being treated. Therapy should be initiated at lower doses (in mg/kg/day), the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, antidepressants or in the treatment of sexual dysfunction, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The activity profile of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

2,3,3a,4,4a,6a,7,7a-Octahydro-2-[3-(3-pyridinyl)-propyl]-4,7-etheno-1H-cyclobut[f]isoindole, dihydrochloride, ¾ hydrate To a stirred solution of 2,3,3a,4,4a,6a,7,7a-octahydro-4,7-etheno-1H-cyclobut[f]isoindole (3 g; 0.017 mol), sodium carbonate (3.5 g, 0.035 mol) and triethylamine 3 mL in 50 mL of dimethylformamide is added 3-pyridinylpropylbromide hydrobromide (4.7 g, 0.017 mol). The reaction mixture is stirred at room temperature overnight, the solvent is removed under vacuum and the remaining solid is extracted in 3×100 mL methylene chloride. The methylene chloride extracts are collected, dried over anhydrous sodium sulfate and evaporated under reduced pressure.

The title compound as free base is separated by preparative HPLC using methanol as the eluent ($R_f$=0.25) and is converted to the hydrochloride salt; m.p. 195°–197° C. (2 g; 40% yield from ethanol-ether 1:1).

Analysis for: $C_{20}H_{24}N_2 \cdot 2$ HCl·¾ $H_2O$: Calculated: C, 60.52; H, 7.44; N, 7.06. Found: C, 60.42; H, 7.39; N, 6.91.

EXAMPLE 2

1-(4-Fluorophenyl)-4-(1,3,3a,4,4a,6a,7,7a-octahydro-4,7-etheno-2H-cyclobut[f]isoindol-2-yl)-1-butanone, hydrochloride, ¾ hydrate To a stirred solution of 2,3,3a,4,4a,6a,7,7a-octahydro-4,7-etheno-1H-cyclobut[f]isoindole (3 g; 0.017 mol), sodium carbonate (3.5 g, 0.035 mol), and triethylamine 3 mL in 50 mL of dimethylformamide is added 4-chloro-4'-fluorobutyrophenone (3.5 g; 0.017 mol). The reaction mixture is stirred at room temperature overnight, the solvent is removed under vacuum and the remaining solid is extracted in 3×100 mL methylene chloride. The methylene chloride extracts are collected, dried over anhydrous sodium sulfate and evaporated under reduced pressure.

The title compound is separated by preparative HPLC using methanol as the eluent and is converted to the hydrochloride salt; m.p. 209°–210° C. (2.5 g; 43% yield).

Analysis for: $C_{22}H_{24}NOF \cdot HCl \cdot$¾ $H_2O$: Calculated: C, 68.21; H, 6.84; N, 3.61 Found: C, 68.02; H, 6.49; N, 3.53

EXAMPLE 3

1-(4-Fluorophenyl)-4-(3,3a,4,5,6,7,8,8a-octahydro-4,8-ethenocyclohepta[c]pyrrol-2(1H)-yl)-1-butanone, hydrochloride, hydrate To a stirred solution of 3,3a,4,5,6,7,8,8a-octahydro-4,8-etheno-cyclohepta[c]pyrrole (3.2 g, 0.019 mol), sodium carbonate (3.5 g, 0.035 mol) and triethylamine 3 mL in 50 mL of dimethylformamide is added 4-chloro-4'-fluorobutyrophenone (3.94 g, 0.019 mol). The reaction mixture is stirred at room temperature overnight, the solvent is removed under vacuum and the remaining solid is extracted in 3×100 mL methylene chloride. The methylene chloride extracts are collected, dried over anhydrous sodium sulfate and evaporated under reduced pressure.

The title compound is separated by preparative HPLC using methanol as the eluent and is converted to the hydrochloride salt; m.p. 177°–179° C. (1.5 g, 24% yield).

Analysis for: $C_{21}H_{26}NOF \cdot HCl \cdot H_2O$: Calculated: C, 66.05; H, 7.60; N, 3.67. Found: C, 65.85; H, 7.0; N, 3.77.

EXAMPLE 4

2,3,3a,4,4a,5,6,6a,7,7a-Decahydro-2-[2-(2-quinolinyl)ethyl]-4,7-etheno-2H-cyclobut[f]isoindole, dihydrochloride, hydrate A mixture of 2,3,3a,4,4a,5,6,6a,7,7a-decahydro-4,7-etheno-2H-cyclobut[f]isoindole (5.0 g, 0.028 mol), 2-vinylquinoline (7.75 g, 0.5 mol) and 2 mL of glacial acetic acid is refluxed for 48 hours in 150 mL of methanol. The solvent is removed under vacuum and the residue is dissolved in methylene chloride. The methylene chloride extract is washed with a saturated solution of sodium carbonate and water respectively, dried over anhydrous sodium sulfate and evaporated under reduced pressure. The title compound is separated by preparative HPLC using methanol as the eluent and is converted to the dihydrochloride salt; m.p. 128°–130° C. (5 g, 54% yield).

Analysis for: $C_{23}H_{26}N_2 \cdot 2\ HCl \cdot H_2O$: Calculated: C, 65.55; H, 7.12; N, 6.65. Found: C, 65.57; H, 7.4; N, 6.17.

EXAMPLE 5

2,3,3a,4,4a,6a,7,7a-Octahydro-2-[2-(2-pyridinyl)ethyl]-4,7-etheno-1H-cyclobut[f]isoindole, dihydrochloride, hemihydrate A mixture of 2,3,3a,4,4a,6a,7,7a-octahydro-4,7-etheno-1H-cyclobut[f]isoindole (2.5 g, 0.014 mol), 2-vinylpyridine (3 g, 0.03 mol) and 2 mL of glacial acetic acid is refluxed for 48 hours in 150 mL of methanol. The solvent is removed under vacuum and the residue is dissolved in methylene chloride. The methylene chloride extract is washed with a saturated solution of sodium carbonate and water respectively, dried over anhydrous sodium sulfate and evaporated under reduced pressure. The title compound is separated by preparative HPLC using methanol as the eluent and is converted to the dihydrochloride salt, m.p. 173°–174° C. (2 g, 51% yield).

Analysis for: $C_{19}H_{22}N_2 \cdot 2\ HCl \cdot \frac{1}{2}\ H_2O$: Calculated: C, 63.77; H, 7.41; N, 7.83. Found: C, 63.83; H, 7.82; N, 7.72.

EXAMPLE 6

2,3,3a,4,4a,5,6,6a,7,7a-Decahydro-2-[2-(2-pyridinyl)ethyl]-4,7-etheno-1H-cyclobut[f]isoindole, dihydrochloride, ¼ hydrate A mixture of 2,3,3a,4,4a,5,6,6a,7,7a-decahydro-4,7-etheno-1H-cyclobut[f]isoindole (5 g, 0.028 mol), 2-vinylpyridine (5.25 g, 0.05 mol) and 2 mL of glacial acetic acid is refluxed for 48 hours in 150 mL of methanol. The solvent is removed under vacuum and the residue is dissolved in methylene chloride. The methylene chloride extract is washed with a saturated solution of sodium carbonate and water respectively, dried over anhydrous sodium sulfate and evaporated under reduced pressure. The title compound is separated by preparative HPLC using methanol as the eluent and is converted to the dihydrochloride salt, m.p. 173°–174° C. (5 g, 63.7% yield).

Analysis for: $C_{19}H_{24}N_2 \cdot 2\ HCl \cdot \frac{1}{4}\ H_2O$: Calculated: C, 63.77; H, 7.41; N, 7.83. Found: C, 63.83; H, 7.82; N, 7.72.

EXAMPLE 7

2,3,3a,4,4a,6a,6,7,7a-Octahydro-2-[2-(2-quinolinyl)ethyl]-4,7-etheno-1H-cyclobut[f]isoindole, dihydrochloride, 1¼ hydrate A mixture of 2,3,3a,4,4a,6a,7,7a-octahydro-4,7-etheno-1H-cyclobut[f]isoindole (2.59 g, 0.014 mol), 2-vinylquinoline (4.5 g, 0.03 mol) and 2 mL glacial acetic acid is refluxed for 48 hours in 150 mL of methanol. The solvent is removed under vacuum and the residue is dissolved in methylene chloride. The methylene chloride extract is washed with a saturated solution of sodium carbonate and water respectively, dried over anhydrous sodium sulfate and evaporated under reduced pressure. The title compound is separated by preparative HPLC using methanol as the an eluent and is converted to the dihydrochloride salt, m.p. 149°–150° C. (2.5 g, 54.4% yield).

Analysis for: $C_{23}H_{24}N_2 \cdot 2\ HCl \cdot 1\frac{1}{4}\ H_2O$: Calculated: C, 65.17; H, 6.72; N, 6.61. Found: C, 65.08; H, 6.54; N, 6.38.

EXAMPLE 8

3-[3-[4-(3-Chlorophenyl)-1-piperazinyl]propyl]-3-azabicyclo[3.2.2]nonane, dihydrochloride To a stirred solution of 3-azabicyclo[3.2.2]nonane (4 g, 0.032 mol), sodium carbonate (4 g, 0.045 mol) and triethylamine 3 mL in 50 mL of dimethylformamide is added 4-(3-chlorophenyl)-1-piperazinylpropylchloride hydrochloride (4 g, 0.0115 mol). The reaction mixture is stirred at room temperature overnight, the solvent is removed under vacuum and the remaining solid is extracted in 3×100 mL methylene chloride. The methylene chloride extracts are collected, dried over anhydrous sodium sulfate and evaporated under reduced pressure.

The title compound is separated by preparative HPLC using methanol as the eluent and is converted to the hydrochloride salt; m.p. >280° C. (1 g; 24.5% yield).

Analysis for: $C_{21}H_{32}N_3Cl \cdot 2\ HCl$: Calculated: C, 58.0; H, 7.82; N, 9.67. Found: C, 57.81; H, 7.77; N, 9.46.

EXAMPLE 9

2-[3-[4-(3-Chlorophenyl)-1-piperazinyl]propyl]-2,3,3a,4,4a,5,6,7,7a-decahydro-4,7-etheno-1H-cyclobut[f]isoindole, trihydrochloride, dihydrate To a stirred solution of 2,3,3a,4,4a,5,6,6a,7,7a-decahydro-4,7-etheno-1H-cyclobut[f]isoindole (2 g, 0.0115 mol), sodium carbonate (4.6 g, 0.046 mol) and triethylamine 3 mL in 50 mL of dimethylformamide is added 4-(3-chlorophenyl)-1-piperazinylpropylchloride hydrochloride (4 g, 0.0115 mol). The reaction mixture is stirred at room temperature overnight, the solvent is removed under vacuum and the remaining solid is extracted in 3×100 mL methylene chloride. The methylene chloride extracts are collected, dried over anhydrous sodium sulfate and evaporated under reduced pressure.

The title compound is separated by preparative HPLC using methanol as the eluent and is converted to the hydrochloride salt; m.p. 270°–272° C. (1 g, 21% yield).

Analysis for: $C_{25}H_{34}N_4Cl \cdot 2\ HCl \cdot 2\ H_2O$: Calculated: C, 53.85; H, 7.36; N, 7.54. Found: C, 53.74; H, 6.72; N, 7.47.

EXAMPLE 10

1-(4-Fluorophenyl)-4-(3,3a,4,4a,5,5a,6,6a-octahydro-4,6-ethenocycloprop[f]isoindol-2-(1H)-yl)-1-butanone, hydrochloride, sesquihydrate To a stirred solution of 3,3a,4,4a,5,5a,6,6a-octahydro-4,6-ethenocycloprop[f]isoindol (1.75 g, 0.011 mol), sodium carbonate (3.5 g, 0.035 mol) and triethylamine 3 mL in 50 mL of dimethylformamide is added 4-chloro-4'-fluorobutyrophenone (3.9 g, 0.019 mol). The reaction mixture is stirred at room temperature overnight, the solvent is removed under vacuum and the remaining solid is extracted in 3×200 mL methylene chloride. The methylene chloride extracts are collected, dried over anhydrous sodium sulfate and evaporated under reduced pressure.

The title compound is separated by preparative HPLC using methanol as the eluent and is converted to the hydrochloride salt; m.p. 190°–191° C. (1.3 g, 23% yield).

Analysis for: $C_{21}H_{24}FNO \cdot HCl \cdot 1\frac{1}{2} H_2O$: Calculated: C, 64.86; H, 7.20; N, 3.60. Found: C, 65.31; H, 6.86; N, 3.73.

EXAMPLE 11

4-(1,3,3a,4,4a,5,6,6a,7,7a-Decahydro-4,7-etheno-1H-cyclobut[f]isoindol-2-yl)-1-(4-fluorophenyl)-1-butanone, hydrochloride To a stirred solution of 2,3,3a,4,4a,5,6,6a,7,7a-decahydro-4,7-etheno-2H-cyclobut[f]isoindole (2.59 g, 0.014 mol), sodium carbonate (3.5 g, 0.035 mol) and triethylamine 3 mL in 50 mL of dimethylformamide is added 4-chloro-4'-fluorobutyrophenone (3.94 g, 0.019 mol). The reaction mixture is stirred at room temperature overnight, the solvent is removed under vacuum and the remaining solid is extracted in 3×100 mL methylene chloride. The methylene chloride extracts are collected, dried over anhydrous sodium sulfate and evaporated under reduced pressure.

The title compound is separated by preparative HPLC using methanol as the eluent and is converted to the hydrochloride salt; m.p. 209°-210° C. (1.8 g, 24% yield).

Analysis for: $C_{22}H_{26}FNO \cdot HCl$: Calculated: C, 70.50; H, 7.19; N, 3.72. Found: C, 69.61; H, 7.49; N, 4.0.

EXAMPLE 12

3-[2-(2-Quinolinyl)ethyl]-3-azabicyclo[3.2.2]nonane, dihydrochloride, dihydrate

A mixture of 3-azabicyclo[3.2.2]nonane (4 g, 0.032 mol), 2-vinylquinoline (7.7 g, 0.05 mol) and 2 mL of glacial acetic acid is refluxed for 48 hours in 150 mL of methanol. The solvent is removed under vacuum and the residue is dissolved in methylene chloride. The methylene chloride extract is washed with a saturated solution of sodium carbonate and water respectively, dried over anhydrous sodium sulfate and evaporated under reduced pressure. The title compound is separated by preparative HPLC using methanol as the eluent and is converted to the dihydrochloride salt; m.p. 195°-197° C. (5 g, 45% yield).

Analysis for: $C_{19}H_{24}N_2 \cdot 2 HCl \cdot 2 H_2O$: Calculated: C, 58.61; H, 7.71; N, 7.19. Found: C, 59.01; H, 7.30; N, 7.27.

EXAMPLE 13

3-[3-[4-(2-Methoxyphenyl)-1-piperazinyl]propyl]-3-azabicyclo[3.2.2]nonane, trihydrochloride, ¾ hydrate To a stirred solution of 3-azabicyclo[3.2.2]nonane (1.1 g, 0.0088 mol), sodium carbonate (1 g, 0.0094 mol), and triethylamine 4 mL in 50 mL of dimethylformamide is added 4-(2-methoxyphenyl)-1-piperazinylpropylchloride dihydrochloride (3.0 g, 0.0088 mol). The reaction mixture is stirred at room temperature overnight, the solvent is removed under vacuum and the remaining solid is extracted with 3×100 mL of methylene chloride. The methylene chloride extracts are collected, dried over anhydrous sodium sulfate and evaporated under reduced pressure.

The title compound is separated by preparative HPLC. It is converted to the hydrochloride salt; m.p. 252°-254° C. (0.9 g, 24.3% yield).

Analysis for: $C_{22}H_{35}N_3O \cdot 3 HCl \cdot \frac{3}{4} H_2O$: Calculated: C, 55.0; H, 8.22; N, 8.75. Found: C, 54.94; H, 7.71; N, 8.3.

EXAMPLE 14

The ex vivo inhibition of 5-$HT_{1A}$ serotonin receptor binding assay is used to determine whether the test compounds can cross the blood-brain barrier and affect the receptor in question and to give an indication of buspirone-like activity.

The assay is carried out as follows:

Several groups of rats (4–6 rats/group) are injected with test compound or the appropriate vehicle. Thirty minutes later, unless otherwise noted, rats are decapitated and their brains removed. Various brain regions are dissected and rapidly frozen and maintained at −70° C. until used.

Hippocampal tissue is dissected and homogenized on ice in 40 vols of buffer (50 mM Tris HCl, pH=7.7) using a Polytron homogenizer at setting 5 for 3×15 sec bursts. The homogenate is then centrifuged at 20,000 rpm (RC5-B; 40,000 g) and the supernatant discarded. The pellet is resuspended in 40 vols of the same buffer and incubated at 37° C. for 10 minutes to aid in the removal of endogenous serotonin. The homogenate is then centrifuged (as above) and the supernatant discarded. The pellet is then resuspended in 100 vols of buffer B (50 mM Tris HCl, pH=7.7 containing 0.1% ascorbate, 10 μM pargyline and 4 mM $CaCl_2$) and sonicated. An aliquot is taken for protein determination by the Lowry method and the remainder stored frozen at −70° C. until used.

The homogenate (50 μl; 0.4–0.6 mg protein/sample) is incubated with 100 μl (1.5–1.8 nM) $^3$H-8-hydroxy-2-(di-n-propylamino)tetraline in a final volume of 2 ml of buffer for 10 minutes at 37° C. At the end of the incubation, 3 ml of cold buffer A are added to each tube, and the contents rapidly filtered through Whatman GF/B glass filters. The filters are then rapidly washed 2 times with 3 ml of the same buffer, placed in scintillation vials, and shaken for 15 minutes with 10 ml of Hydrofluor (National Diagnostics) scintillation cocktail. The vials are then counted in a Packard 460 CD scintillation counter.

Specific binding is calculated for each of the treatment protocols and is defined as total binding less binding in the presence of excess unlabeled serotonin (1 μM). Specific binding obtained in vehicle-treated rats is compared to that obtained in animals receiving a single or various doses of test compound and expressed as percent of control. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-}8\text{-}OH\ DPAT]}{K_D}}$$

where $K_D = 1.8$ nm for 8-OH DPAT binding in hippocampus

The use of several doses of test compound also permits the calculation of an $ID_{50}$ value, i.e. an inhibitory dose that displaces 50% of the specific binding ex vivo.

under these conditions, buspirone (30 mg/kg) displaced 46% of specific $^3$H-8-OH-DPAT binding from hippocampal membranes.

When tested in this assay, the compounds of the invention gave the following results.

TABLE 1

| Compound of Example No. | % Inhibition of 8-OH DPAT Binding at 1 μm |
|---|---|
| 3 | 61 |
| 4 | 97 |
| 6 | 89 |
| 7 | 46 |
| 8 | 82 |
| 12 | 30 |
| 13 | 94 |

The results show that compounds of the invention have a moderate to extremely strong affinity for binding to the 5-$HT_{1A}$ receptor site, evidencing a high potential for buspirone-like activity.

EXAMPLE 15

The compounds of the invention are also studied for their ability to inhibit limbic D-2 dopamine receptor binding. This in vitro assay measures the ability of the compounds tested to bind to the dopamine receptor sites. Those compounds which exhibit a weak binding effect have a low liability to display potential extrapyramidal side effects.

The test is carried out as follows:

Several rats are decapitated and the brains are rapidly removed. Limbic brain tissue (nucleus accumbens, septal area, olfactory tubercle) is dissected and homogenized on ice in 9 volumes of buffer (50 mM Tris-HCl, 120 mM NaCl, 5 mM KCl, 1 mM $CaCl_2$, 1 mM $MgCl_2$, 0.1% L-ascorbic acid, 10 μM pargyline HCl, pH 7.1) using a Polytron homogenizer at setting 5 for three 15-sec bursts. The homogenate is then diluted 4-fold with buffer and centrifuged at 30,000×g for 20 minutes, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

Thirty μL of the homogenate (0.2–0.3 mg protein/sample) are incubated with 0.3 nM $^3$H-spiroperidol (New England Nuclear) and various concentrations of test drug in a final volume of 1 ml of the above buffer for 10 minutes in a 37° C. water bath. At the end of the incubation, 3 ml of cold 50 mM Tris-Hcl, pH 7.7, are added to each tube, and the contents are rapidly vacuum-filtered through Whatman GF/B glass-fiber filters. The filters are then rapidly washed 3 times with 3 ml of the same buffer, placed in scintillation vials, and shaken for 15 minutes with 10 ml of Hydrofluor (National Diagnostics) scintillation cocktail. The vials are then counted in a Packard 460 CD scintillation counter.

Specific binding is defined as total binding less binding in the presence of 1 μM (+)butaclamol. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H\text{-Spiroperidol}]}{K_D}}$$

where $K_D = 0.3$ nM for spiroperidol binding

| Standard Compounds | $K_i$ and 95% confidence interval |
|---|---|
| Haloperidol | 4.0 (3.0–5.6) nM |
| Clozapine | 34 (23–54) nM |
| Fluphenazine | 4.5 (3.6–5.6) nM |
| Sulpiride | 376 (174–5000) nM |

The results of testing of some of the compounds of the invention in this assay are presented in Table 2.

TABLE 2

| Compound of Example No. | % Inhibition of $H^3$-Spiroperidol Binding at 1 μm |
|---|---|
| 3 | 100 |
| 4 | 17 |
| 6 | 3 |
| 8 | 11 |
| 9 | 40 |
| 10 | 93 |
| 13 | 55 |

The results show that compounds of the invention display a range of inhibitory effects, with some compounds exhibiting a very weak inhibitory effect, evidencing a low potential for extrapyramidal side effects.

What is claimed is:

1. A compound having the formula

R⌒N—$(CH_2)_m$—A wherein R represents

[structures with X, Y, $(CH_2)_n$]

where
X is lower alkylene, vinylene or O;
Y is lower alkylene or vinylene;
m is 1–3;
n is 2–4;
A is pyridinyl or pyridinyl substituted with lower alkyl, lower alkoxy, halo, cyano, nitro or trifluoromethyl; or a pharmacologically acceptable salt thereof.

2. The compound of claim 1, having the name 2,3,3a,4,4a,6a,7,7a-octahydro-2-[3-(3-pyridinyl)propyl]-4,7-etheno-1H-cyclobut[f]isoindole.

3. The compound of claim 1, having the name 2,3,3a,4,4a,6a,7,7a-octahydro-2-[2-(2-pyridinyl)ethyl]-4,7-etheno-1H-cyclobut[f]isoindole.

4. The compound of claim 1, having the name 2,3,3a,4,4a,5,6,6a,7,7a-decahydro-2-[2-(2-pyridinyl)ethyl]-4,7-etheno-1H-cyclobut[f]isoindole.

* * * * *